US00PP12112P2

(12) United States Plant Patent
Walden

(10) Patent No.: US PP12,112 P2
(45) Date of Patent: Oct. 2, 2001

(54) MINIATURE ROSE PLANT NAMED 'JACMIRYL'

(75) Inventor: John K. Walden, Burlington, WA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/455,212

(22) Filed: Dec. 6, 1999

(51) Int. Cl.[7] ..... A01H 5/00
(52) U.S. Cl. ..... Plt./118
(58) Field of Search ..... Plt./118, 125

*Primary Examiner*—Howard J. Locker
(74) *Attorney, Agent, or Firm*—Klarquist Sparkman Campbell Leigh & Whinston, LLP

(57) ABSTRACT

A miniature rose plant having dwarf, full plant habit; pointed ovoid buds; high centered, rich yellow flowers; abundant, dark green, glossy foliage; and resistance of foliage to powdery mildew and rust.

1 Drawing Sheet

The present invention relates to a new and distinct variety of rose plant of the miniature rose class which was originated by me by crossing the variety 'JACyepat' (not patented), with the variety 'JACimin' (U.S. Plant Pat. No. 8,850).

The primary objective of this breeding was to produce a new rose variety having a dwarf plant habit displaying yellow, two inch, high centered flowers, pointed ovoid buds and dark green, glossy foliage with resistance to powdery mildew and rust. The objective was substantially achieved, along with other desirable improvements, as evidenced by the following unique combination of characteristics that are outstanding in the new variety and that distinguish it from its parents, as well as from all other varieties of which I am aware:

1. A dwarf, miniature rose plant habit;
2. Pointed ovoid flower buds;
3. Two inch, high centered, open blooms;
4. Dark green, glossy foliage; and
5. Resistance to powdery mildew and rose rust.

Asexual reproduction of this new variety by cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACyepat' (not patented).

*Pollen parent.*—'JACimin' (U.S. Plant Pat. No. 8,850).

Classification:

*Botanical.*—*Rosa hybrida.*

*Commercial.*—Miniature rose.

FLOWER

Observations made in September, 1999, from specimens grown in a garden environment at Somis, Calif.

Blooming habit: Recurrent.

Bud:

*Size.*—About ¾ inch long when the petals start to unfurl.

*Form.*—The bud form is pointed ovoid.

*Color.*—When sepals first divide, bud color is Yellow Group 13A. When half blown, the upper sides of the petals are Yellow-Orange Group 14B; and the lower sides of the petals are Yellow-Orange Group 14B.

*Sepals.*—Color: Near Yellow-Green Group 146B. Surface texture: Smooth to slightly rough and glandular. There are three normally appendaged sepals. There are two unappendaged sepals with hairy edges.

*Receptacle.*—Color: Near Yellow-Green Group 144A. Shape: Funnel. Size: Small, about 5/16 inch×¼ inch. Surface: Smooth.

*Peduncle.*—Length: Short, average about ⅞ inch. Surface: Rough; glandular. Color: Yellow-Green Group 145A. Strength: Stiff; erect.

Bloom:

*Size.*—Small. Average open size is two inches.

*Borne.*—Mostly singly and in small, rounded clusters of three to five blooms.

*Stems.*—Strength: Normal. Average length is about eight to nine inches.

*Form.*—When first open: High centered. Permanence: Retains its form to the end; outer petal edges curl slightly.

*Petalage.*—Number of petals under normal conditions: 30 to 35.

*Color.*—The upper sides of the petals are Yellow Group 12A. The reverse sides of the petals are Yellow Group 12B. The base of the petals is Yellow Group 12A. The major color on the upper side is Yellow Group 12A.

*Variegations.*—None.

*Discoloration.*—The general tonality at the end of the first day: Yellow Group 12A. At the end of the third day: Lightening toward Yellow Group 12B. With further aging, continued lightening of color to between yellow Group 10B and 10C, and then finish near Yellow Group 11D before drying.

*Fragrance.*—Slight; light, fruity and spicy.

Petals:

*Texture.*—Leathery.

*Shape.*—Round to oval.

*Form.*—Edges moderately quilled.

*Arrangement.*—Imbricated (regularly arranged). Petaloids in the center are many (six to eight); large.

*Persistence.*—Petals hang on and dry.

*Lastingness.*—On the plant: Long (about nine to ten days). As a cut flower: Not tested.

Reproductive parts:

*Anthers.*—Size: Medium. Quantity: Many. Color: Between Yellow Group 11A and Yellow Group 11B. Arrangement: Regular around styles.

*Filaments.*—Color: Near Yellow Group 12A.

*Pollen.*—Color: Near Yellow-Orange Group 22A.

*Styles.*—Color: Red Group 45A.

*Stigmas.*—Color: Yellow-Orange Group 15D.

Plant:

*Form.*—Bush.

*Growth.*—Vigorous; dwarf; upright; branching. At maturity, height is 20 to 22 inches, width is 24 to 26 inches.

Foliage: Number of leaflets on normal mid-stem leaves: Five or seven.

*Size.*—Small (2¾ inches long×1⅝ inches wide).

*Quantity.*—Abundant.

*Color.*—New foliage: Upper surfaces: Near Yellow-Green Group 146B, and Greyed-Purple Group 184A at margins. Lower surfaces: Greyed-Purple Group 184A, rapidly turning green. Old foliage: Upper surface: Green Group 137B. Lower surface: Near Yellow-Green Group 146B.

Leaflets:

*Shape.*—Broadly oval; pointed oval.

*Texture.*—Glossy; smooth.

*Edge.*—Serrated.

*Serration.*—Single.

*Petiole rachis.*—Color. Yellow-Green Group 146B.

*Petiole underside.*—With prickles; Yellow-Green Group 146C in color.

*Stipules.*—Short (about ⅜ to 7/16 inch), lightly bearded.

*Disease resistance.*—Foliage is resistant to rust and tolerant to blackspot under normal growing conditions. Foliage is also resistant to powdery mildew under normal growing conditions, but under severe conditions plant may exhibit powdery mildew on peduncles only.

Wood:

*New wood.*—Color: Yellow-Green Group 146C. Bark: Smooth.

*Old wood.*—Color: Yellow-Green Group 146B. Bark: Smooth.

Prickles:

*Quantity.*—On main canes from base: Ordinary. On laterals from main canes: Ordinary.

*Form.*—Short (¼ inch to 5/16 inch); straight.

*Color when young.*—Greyed-Red Group 181B.

*Color when mature.*—Between Greyed-Orange Group 165A and Greyed-Orange Group 165B.

Small prickles:

*Quantity.*—On main stalks: None. On laterals: None.

I claim:

1. A new and distinct variety of rose plant of the miniature class, substantially as herein shown and described, characterized particularly by its dwarf, full plant habit; pointed ovoid buds; high centered, rich yellow flowers; abundant, dark green, glossy foliage; and resistance of foliage to powdery mildew and rust.

* * * * *

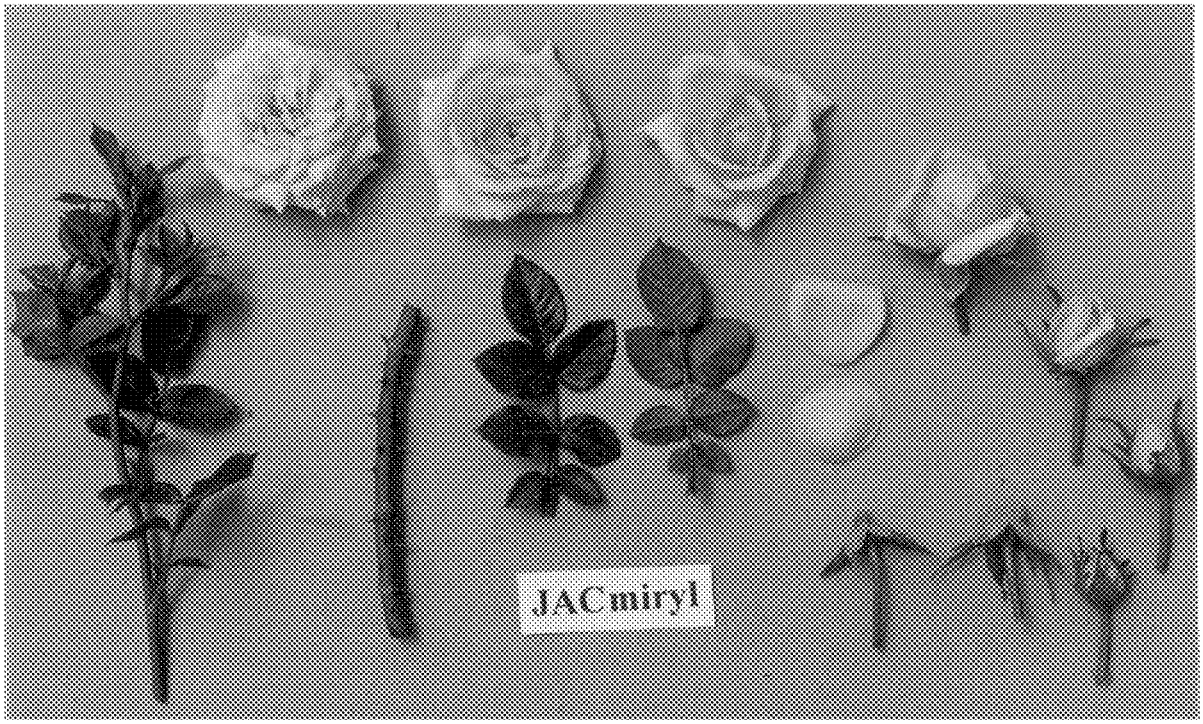
JACmiry1